United States Patent [19]

Strickler

[11] 4,034,071

[45] July 5, 1977

[54] IMMUNOASSAY PROCEDURES

[75] Inventor: Herbert S. Strickler, Pittsburgh, Pa.

[73] Assignee: Allegheny General Hospital, Pittsburgh, Pa.

[22] Filed: Jan. 26, 1976

[21] Appl. No.: 652,302

[52] U.S. Cl. .................................. 424/1; 23/230 B; 23/230.6; 252/447; 424/12
[51] Int. Cl.$^2$ ................... G01N 33/00; G21H 5/02; B01J 1/22
[58] Field of Search ................. 424/1, 1.5, 12, 357; 23/230 B, 230.6; 252/447, 461

[56] References Cited

UNITED STATES PATENTS

| 1,519,470 | 12/1924 | Wilson et al. | 252/447 |
|---|---|---|---|
| 2,112,931 | 4/1938 | Schulze | 252/447 |
| 2,470,688 | 5/1949 | Carter | 252/447 |
| 3,442,819 | 5/1969 | Herbert | 424/12 |
| 3,666,854 | 5/1972 | Eisentraut | 424/1 |
| 3,768,979 | 10/1973 | Mead et al. | 250/303 |
| 3,816,076 | 6/1974 | Backer | 23/230 B |
| 3,843,775 | 10/1974 | Wolf | 23/230.6 |
| 3,896,217 | 7/1975 | Johnson | 424/1 |

Primary Examiner—Benjamin R. Padgett
Assistant Examiner—Christine M. Nucker
Attorney, Agent, or Firm—Webb, Burden, Robinson & Webb

[57] ABSTRACT

The technique of separating a tagged bound material from the same unbound material in immunoassay procedures is improved by utilizing a clathrate sorbent to carry out the separation. A clathrate sorbent, for example, comprises a mixture of hydrate zinc sulfate and sodium hydroxide which form an inclusion compound with charcoal powder. Charcoal powder has also been combined to form a clathrate sorbent with salts of other metals which produce a gelatinous substance with alkaline hydroxides; e.g., alum with sodium hydroxide. Another example of a clathrate sorbent is magnesium trisilicate combined with the aforementioned zinc preparation.

14 Claims, No Drawings

IMMUNOASSAY PROCEDURES

FIELD OF THE INVENTION

My invention relates to improvements in immunoassay and, more particularly, to the separation of a radioactive or otherwise tagged bound material from an unbound material.

DESCRIPTION OF THE PRIOR ART

Radioimmunoassay (RIA) and similar procedures are a relatively recent development whereby difficult to measure constituents are analyzed through the use of radioisotopes, etc. The general procedure usually requires a specific antibody, a radiolabeled or otherwise tagged antigen, a pure sample of the antigen to serve as a reference standard and means of separating the free antigen from the antibody bound antigen. Competitive binding occurs between the labeled ("tagged") and the unlabeled antigen for a fixed number of antibody binding sites. When equilibrium is reached between the antigen antibody reaction, the free and bound components of the mixture are separated and the relative amounts of each are determined by measuring the radioactivity or other tagging (e.g., fluorescence) of the separated components. This can be done by comparing the results of the unlabeled antigen in the sample to a standard curve prepared from known amounts of the unlabeled antigen.

This separation step is the key to an accurate and timely assay.

Presently, the majority of these separations are performed manually and, of course, these manual procedures are time consuming and prone to error because of the meticulous measurements that are required. Automation of these techniques has taken place but the separation step has continued to lead to pitfalls in automated laboratory RIA equipment.

Charcoal has generally been the sorbent used to make the separation. The various forms of charcoal presently in use tend to plug the automatic equipment, thereby rendering this equipment ineffectual for continuous assay analysis. Therefore, analysts continue to rely on manual procedures rather than risk the continuous flow procedures. The following patents are exemplary of RIA procedures using charcoal and other sorbents in their presently utilized forms. Mead U.S. Pat. No. 3,615,222; Mead et al. U.S. Pat. Nos. 3,721,528 and 3,768,979; Eisentraut U.S. Pat. No. 3,775,615; Eisentraut U.S. Pat. No. 3,666,854; Wolf U.S. Pat. No. 3,843,775; Johnson U.S. Pat. No. 3,896,217.

SUMMARY OF THE INVENTION

I have now found that the inadequacies of automated procedures can be overcome without sacrificing any accuracy in result or delay in analysis. The form of the sorbent which I use permits continuous filtering so that the filtrate can be counted to give an immediate readout of the results. The automation of the technique reduces the turnaround time of these tests and minimizes errors inherent in the procedure.

My improvement provides for the separation of a radioactive or other tag material and untagged bound material from that which has not been bound by utilizing clathrate sorbent. The clathrate sorbent presently preferred is charcoal. The preferred sorbent is composed of a mixture of hydrate zinc sulfate, sodium hydroxide and charcoal powder. This mixture is present in relative amounts of 3 grams of $ZnSO_4 \cdot 7H_2O$, 15 ml. of 1N NaOH, 365 ml of $H_2O$ and 2.48 grams of charcoal powder. The charcoal powder can also be combined to a clathrate sorbent with other salts of metals which produce a gelatinous substance with alkaline hydroxides. Other sorbents such as magnesium trisilicate can also be used.

DESCRIPTION OF THE PREFERRED EMBODIMENTS

A clathrate compound is generally considered as an inclusion complex in which molecules of one substance are completely caged within the other. Specifically, the molecules of one component are held within the crystal lattice framework of the other component. The larger molecule remains dominant and the inclusion molecule is positioned in cavities of the larger molecule defined by the larger molecule's crystal lattice. This spotty attachment allows for exposure of substantial surface area of the dominant molecules.

I have found that by using charcoal and other sorbents, I have arrived at a substance which retains the absorptive qualities of the sorbent while, at the same time, making it free flowing so that it can be used in continuous flow separations. I have successfully prepared a clathrate charcoal composition by mixing the following chemicals and substances:

EXAMPLE I

Preparation of clathrate compound formed of charcoal with zinc hydroxide.

3 grams $ZnSO_4 \cdot 7H_2O$
15 ml 1N NaOH
365 ml $H_2O$
2.48 grams charcoal powder of the type presently used in RIA procedures.

The mixture is made as follows: The hydrate zinc sulfate is dissolved in the water. Then the sodium hydroxide is added and the preparation is thoroughly mixed and the charcoal powder is added. The pH of the preparation is then measured with a glass electrode. If it is below 6.8, more sodium hydroxide is added dropwise until pH 6.8 is attained. The charcoal powder is thereafter added. The entire procedure is carried out at room temperature. The preparation is stored in the refrigerator.

I have also successfully formed other clathrate sorbents.

EXAMPLE II

Clathrate magnesium trisilicate.

The same weight (2.48 grams) of magnesium trisilicate (U.S.P. grade) is added to the chemicals of Example I instead of the RIA grade charcoal.

EXAMPLE III

Preparation of a clathrate compound formed of charcoal with aluminum hydroxide. Ammonium alum, N. F., having twice the number of moles than the hydrate zinc sulfate of Example I was dissolved and heated with 40/15 times the amount of sodium hydroxide to drive off the ammonia. The mixture was cooled, diluted to the usual volume, and the charcoal was added in the normal manner. The pH was adjusted, if necessary, to 6.8.

I have successfully employed the clathrate charcoal in an automated RIA assay equipment. This has permitted the use of continuous flow filtering which speeds up the assay time, see Table 1. As a secondary benefit, I have noted that the clathrate charcoal has substantially improved precipitation properties and thus can speed up centrifugation where such procedures are necessary for assay.

Table 1 illustrates the amount of radioactivity bound to a fixed amount of antibody. Duplicate results show reproducibility. The decrease in radioactivity is correlated with increase in the amount of untagged antigen.

TABLE 1

| Digoxin Assay | |
|---|---|
| ng/ml | Radioactivity Bound* |
| 0 | 55.2 |
| 0 | 56.9 |
| 0.5 | 51.1 |
| 1.0 | 48.4 |
| 1.0 | 49.6 |
| 2.0 | 43.2 |
| 2.0 | 44.2 |
| 3.0 | 39.5 |
| 3.0 | 40.5 |
| 5.0 | 34.6 |
| 5.0 | 35.6 |

*Recorder chart readings corrected for interaction.

Table 2 demonstrates the results obtained during a five minute centrifugation with clathrate charcoal in a titer demonstration.

TABLE 2

| | Digoxin Assay | |
|---|---|---|
| ng/ml | Antibody | % Binding |
| 0 | 1x | 76.8 |
| 0 | 1x | 77.6 |
| 0 | ½x | 65.6 |
| 0 | ½x | 66.0 |
| 5 | ½x | 34.0 |
| 5 | ½x | 34.0 |
| 0 | ¼x | 43.9 |
| 0 | ¼x | 45.5 |
| 5 | ¼x | 22.6 |
| 5 | ¼x | 23.6 |

I have thus been able to automate completely the assay of serum digoxin through a continuous flow procedure. Specifically, the samples plus the radioactive reagent are picked up and mixed with an antiserum and incubated in the delay coil for one half hour. The clathrate charcoal made in accordance with my invention is then added, mixed and filtered continuously. The clear filtrate is counted by a two inch crystal, pierced horizontally in a rate meter with associated recorder, power supply amplifier and spectrometer. All of this latter equipment is known and presently used and does not form a part of my invention.

In the digoxin test, I obtained confidence limits of ±3.9%. I have also had conducted thyroxine assays using my method and have obtained confidence limits of ±4.9. These results compare favorably with the standard manual techniques presently in use.

It is presently believed that the hydrate zinc sulfate, as well as other metal salts, and the sodium hydroxide or other alkaline hydroxide, react to form a zinc or other hydroxide which is held in lattice sites of the material. The gelatinous hydroxide acts somewhat like a lubricant, thereby preventing the charcoal from clogging the equipment necessary for the automatic RIA or other immunoassay procedures. At the same time, effectiveness of the charcoal or other sorbent used in separating the bound from the free material is not affected because of the large surface area of the charcoal or other sorbent which remains in contact with the mixture to be separated.

I claim:

1. In an immunoassay procedure, including the step of separating within a mixture a bound untagged substance and a bound tagged same substance from unbound substance and unbound tagged same substance by selectively absorbing the unbound portions, the improvement comprising subjecting said mixture to a clathrate compound having a host substance and an inclusion substance to carry out the separation, wherein a sorbent is the host substance.

2. The improvement of claim 1, said sorbent being charcoal.

3. The improvement of claim 1, said sorbent being selected from the group consisting of charcoal powder as the host substance with zinc hydroxide as the inclusion substance, charcoal powder as the host substance with aluminum hydroxide as the inclusion substance and magnesium trisilicate as the host substance with zinc hydroxide as the inclusion substance.

4. The improvement of claim 2, said clathrate charcoal consisting essentially of a mixture of zinc sulfate, sodium hydroxide, water and charcoal powder.

5. The improvement of claim 4, said mixture being present in relative amounts of 3 grams of $ZnSO_4 \cdot 7H_2O$, 15 ml of 1N NaOH, 365 ml of $H_2O$ and 2.48 grams of charcoal powder.

6. The improvement of claim 2, said clathrate charcoal consisting essentially of a mixture of alum, sodium hydroxide, water and charcoal powder.

7. The improvement of claim 1, said sorbent being magnesium trisilicate.

8. A procedure for separating within a first mixture a bound untagged substance and a bound tagged same substance from unbound substance and unbound tagged same substance comprising adding to said first mixture a compound formed from a mixture of hydrate zinc sulfate, sodium hydroxide, water and charcoal powder to form a second mixture and filtering said second mixture to effect the separation.

9. In an automated system for performing immunoassays in which a bound untagged substance and a bound tagged same substance are separated from unbound substance and unbound tagged same substance within a mixture by selectively absorbing the unbound portions, the improvement comprising:
   A. adding to the mixture to be separated a clathrate charcoal;
   B. mixing the clatherated charcoal and the mixture; and
   C. continuously filtering to obtain the bound untagged substance and bound tagged same substance as a filtrate.

10. The improvement of claim 9, said clathrate charcoal consisting essentially of a mixture of zinc sulfate, sodium hydroxide, water and charcoal powder.

11. The improvement of claim 10, said mixture being present in the relative amounts of 3 grams of $ZnSO_4 \cdot 7H_2O$, 15 ml of 1N NaOH, 365 ml of $H_2O$ and 2.48 grams of charcoal powder.

12. A clathrate charcoal inclusion complex product comprising molecules of charcoal powder as a host substance having a crystal lattice and molecules of an inclusion substance formed by the reaction of hydrate zinc sulfate, sodium hydroxide and water, said inclusion substance retained in said crystal lattice to form said product.

13. The product of claim 12, said product formed by a mixture being present in the relative amounts of 3 grams $ZnSO_4 \cdot 7H_2O$, 15 ml of 1N NaOH, 365 ml of $H_2O$ and 2.48 grams of charcoal powder.

14. In an automated system for performing immunoassays wherein a binding agent is mixed with a tagged substance and an amount of untagged same substance to form a mixture having (i) bound tagged substance, (ii) bound untagged substance, (iii) unbound tagged substance, and (iv) unbound untagged substance, the improvement comprising:
   A. adding to the mixture a clathrate charcoal;
   B. allowing the mixture and the clathrate charcoal to remain in contact for an incubation period to permit the absorption of the unbound segments of the mixture by the clathrate charcoal;
   C. continuously filtering the mixture to obtain the bound components as a filtrate; and
   D. determining the amount of bound tagged substance in the filtrate.

* * * * *